United States Patent
Abramovici et al.

(10) Patent No.: US 7,323,493 B1
(45) Date of Patent: Jan. 29, 2008

(54) SOLID PHARMACEUTICAL COMPOSITION CONTAINING BENZOFURAN DERIVATIVES

(75) Inventors: Bernard Abramovici, Juvignac (FR); Jean-Claude Gautier, Clapiers (FR); Jean-Claude Gromenil, Mountbazin (FR); Jean-Marie Marrier, Lattes (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 09/446,601

(22) PCT Filed: Jun. 19, 1998

(86) PCT No.: PCT/FR98/01285

§ 371 (c)(1),
(2), (4) Date: Apr. 3, 2000

(87) PCT Pub. No.: WO98/58643

PCT Pub. Date: Dec. 30, 1998

(30) Foreign Application Priority Data

Jun. 23, 1997 (FR) .................................. 97 07795

(51) Int. Cl.
*A61K 31/343* (2006.01)
(52) U.S. Cl. ........................ 514/469; 514/975; 514/960; 514/467
(58) Field of Classification Search ................ 514/469, 514/467
See application file for complete search history.

(56) References Cited

U.S. PATENT DOCUMENTS

| | | | | |
|---|---|---|---|---|
| 3,248,401 A | | 4/1966 | Tondeur et al. ........... 260/346.2 |
| 4,944,949 A | * | 7/1990 | Story et al. ................. 424/451 |
| 5,100,911 A | | 3/1992 | Binder et al. ............... 514/422 |
| 5,118,707 A | | 6/1992 | Chatterjee et al. .......... 514/469 |
| 5,223,510 A | | 6/1993 | Gubin et al. ................ 514/299 |
| 6,143,778 A | * | 11/2000 | Gautier et al. .............. 514/469 |

FOREIGN PATENT DOCUMENTS

| | | |
|---|---|---|
| EP | 0 338 746 | 10/1989 |
| FR | 2 735 978 | 1/1997 |
| WO | WO88/07996 | 10/1988 |
| WO | WO89/02892 | 4/1989 |
| WO | WO90/02743 | 3/1990 |
| WO | WO94/29289 | 12/1994 |
| WO | WO 97/02031 | 1/1997 |
| WO | WO97/17064 | 5/1997 |

OTHER PUBLICATIONS

Martin-Algarra et al. Effects of polysorbate 80 on amiodarone intestinal absorption in the rat, Jan. 18, 1995, International Journal of Pharmaceutics, vol. 122 pp. 1-8.*
Physicians Desk Reference, on line version htte://www.pdrel.com/pdr/satic.het?path=pdrel/pdr/90401840.htm.*
Martin-Algarra et al. Effects of Polysorbate 80 on Amiodarone Intestinal Absorption in the Rat, 1995, International Journal of Pharmaceutics 122 (1,2) pp. 1-8.*
Chemical Abstracts, vol. 123, No. 8 (Aug. 21, 1995), Abstract No. 93077.
Chemical Abstracts, vol. 121, No. 6 (Aug. 8, 1995), Abstract No. 65480.
Chemical Abstracts, vol. 71, No. 26 (Dec. 29, 1969), Abstract No. 128658.
Derwent Patent Abstract No. 199710.
Derwent Patent Abstract No. 199725.
Gough et al, Hypotensive Action of Commercial Intravenous Amiodarone and Polysorbate 80 In Dogs, J Cardiovasc Pharmacol, vol. 4, No. 3, 1982, pp. 375-380.
Path et al, Effects of Amiodarone With and Without Polysorbate 80 on Myocardial Oxygen Consumption and Coronary Blood Flow During Treadmill Exercise In the Dog, J Cardiovasc Pharmacol, vol. 18, No. 1, 1991, pp. 11-16.

* cited by examiner

*Primary Examiner*—Ardin H. Marschel
*Assistant Examiner*—Donna Jagoe
(74) *Attorney, Agent, or Firm*—Kelly L. Bender

(57) ABSTRACT

The present invention relates to a solid pharmaceutical composition for oral administration characterized in that it comprises a benzofuran derivative with antiarrhythmic activity, or one of the pharmaceutically acceptable salts thereof, as an active principle, and a pharmaceutically acceptable nonionic hydrophilic surfactant optionally in combination with one or more pharmaceutical excipients.

14 Claims, 2 Drawing Sheets

SOLID PHARMACEUTICAL COMPOSITION CONTAINING BENZOFURAN DERIVATIVES

The present invention relates generally to a novel pharmaceutical composition for oral administration containing a benzofuran derivative as active principle.

More precisely, the invention relates to a solid pharmaceutical composition for oral administration containing a benzofuran derivative with anti-arrhythmic activity as active principle.

In the context of the present invention, the expression "benzofuran derivative with antiarrhythmic activity" is understood to denote a benzofuran compound chosen from those described in U.S. Pat. Nos. 3,248,401 and 5,223,510 and European patent EP 338,746, as well as in patent applications WO 88/07996, WO 89/02892, WO 90/02743 and WO 94/29289.

Of all of these compounds, mention may preferably be made of 2-n-butyl-3-[4-(3-di-n-butyl-aminopropoxy)benzoyl]-5-methylsulphonamidobenzofuran or dronedarone and the pharmaceutically acceptable salts thereof described in U.S. Pat. No. 5,223,510, as well as 2-n-butyl-3-(3,5-diiodo-4-diethylaminoethoxybenzoyl)-benzofuran or amiodarone and the pharmaceutically acceptable salts thereof described in U.S. Pat. No. 3,248,401.

Similarly, the expression "solid pharmaceutical composition" is understood to refer essentially to a pharmaceutical composition formed entirely of pulverulent solid ingredients which can be tabletted at room temperature, comprising the active principle and the excipients, these ingredients being essentially in powder form.

Consequently, the so-called semi-solid pharmaceutical compositions, formed of substances in pasty or waxy form when they are brought to moderate temperature (<70° C.), do not form part of the invention.

The antiarrhythmic compounds used in the context of the invention, in particular dronedarone and amiodarone in the form of their hydrochloride, are characterized by low solubility in aqueous medium.

For example, the solubility curve of dronedarone hydrochloride at room temperature and as a function of the pH reveals a maximum solubility around pH values of 3 to 5, of about 1 to 2 mg/ml, but very low solubility at pH values of about 6 to 7, since it is only 10 μg/ml at pH=7.

As regards amiodarone hydrochloride, its solubility at room temperature is from 0.3 to 0.9 mg/ml in the pH range from 3 to 4, and is a few μg/ml at pH=7.

Thus, it is possible to dissolve 400 mg of dronedarone hydrochloride in 200 ml of aqueous medium buffered to pH=4 (aqueous 0.1 M $NaH_2PO_4$ solution).

On the other hand, in this medium diluted to 1/10 with an aqueous solution buffered to pH=7 (aqueous 0.1 M $Na_2HPO_4$ solution), dronedarone hydrochloride precipitates (pH of the final medium: 6.7).

Since these solubility conditions are similar to those recorded in the gastrointestinal tract, it can be assumed that dronedarone hydrochloride risks being subjected, in the stomach, to acidic conditions which are favourable to its solubilization, but, on the other hand, risks encountering a medium of pH=6 to 7 once it enters the intestine, i.e. a non-solubilizing medium in which it will precipitate.

This behaviour in intestinal medium probably makes it possible to explain in vivo the low bio-availability of dronedarone hydrochloride and the differences observed after administration with or without food, since it has been observed that the bio-availability of dronedarone hydrochloride in dogs and in man is increased after the intake of food, in particular fats, which can greatly modify the precipitation kinetics of this active principle and also help to place it in emulsion form.

Since the absorption of food gives rise to the secretion of bile salts, which are anionic surfactants, it appears that this might have a favourable influence on the solubilization of dronedarone hydrochloride.

However, tests carried out to this end showed, in contrast, that this active principle precipitates in the presence of bile salts such as sodium taurocholate.

The development of an oral pharmaceutical composition of dronedarone, of amiodarone or of pharmaceutically acceptable salts thereof, which is capable of avoiding the precipitation of the active principle in neutral medium and of reducing the variability of absorption of this active principle into the plasma, i.e. of providing an acceptable bioavailability independently of the presence of food, remains of fundamental interest.

It has now been found, surprisingly, that the combination of a nonionic hydrophilic surfactant with dronedarone, amiodarone or the pharmaceutically acceptable salts thereof, makes it possible to maintain the solubilization of this active principle in neutral medium and to reduce, in man, its variability of absorption into the blood.

This observation is all the more surprising since preliminary tests carried out on dogs did not make it possible to show that a nonionic hydrophilic surfactant was capable of increasing the fasted bioavailability of dronedarone hydrochloride, and at the same time of reducing the variability of absorption of this active principle into the plasma.

Thus, the invention relates to a solid pharmaceutical composition for oral administration comprising a benzofuran derivative with antiarrhythmic activity, or one of the pharmaceutically acceptable salts thereof, as an active principle, and to a pharmaceutically acceptable nonionic hydrophilic surfactant optionally in combination with one or more pharmaceutical excipients.

This pharmaceutical composition can be in any solid pharmaceutical form which is suitable for oral administration, such as a tablet which may or may not be splittable, a granule, a gelatin capsule or a powder in a unit sachet.

Consequently, another subject of the invention relates to the above oral pharmaceutical composition in tablet, granule, gelatin capsule or powder form.

The nonionic hydrophilic surfactant used in the composition of the invention can be chosen from:

ethyleneoxide/propyleneoxide copolymers referred to hereinbelow as poloxamers, such as poloxamer 124 sold under the brand name Synperonic® PE/L44; poloxamer 188 sold under the brand name Pluronic® F68 or Synperonic® PE/F68; poloxamer 237 sold under the brand name Pluronic® F87 or Synperonic® PE/F87; poloxamer 338 sold under the brand name Synperonic® PE/F108 or poloxamer 407 sold under the brand name Pluronic® F127, Synperonic® PE/F127 or Lutrol® F127.

polyethoxylated castor oils such as those sold under the brand name Cremophor® RH40.

ethoxylated polysorbates, such as polysorbate 20, polysorbate 40, polysorbate 60 and polysorbate 80 sold respectively under the brand names Tween® 20, Tween® 40, Tween® 60 and Tween® 80.

or alternatively polyethylene hydroxystearates such as polyethylene hydroxystearate 660 sold under the brand name Solutol® HS15.

As preferred surfactant, mention may be made of poloxamer 407.

Usually, the nonionic hydrophilic surfactant in question is incorporated into the solid compositions of the invention in a proportion of from 1% to 50% by weight relative to the active principle in base form, irrespective of the unitary or non-unitary pharmaceutical form adopted for packaging them.

For the preparation of solid compositions in tablet form or packaged in gelatin capsule form, from 1% to 20% by weight of surfactant relative to the active principle in base form, preferably from 5% to 15%, will be used, for example.

As a non-limiting guide, the amount of active principle can range from 50 to 500 mg per administration unit in tablet form, which entails the incorporation of an amount of surfactant of between 0.5 and 100 mg. These amounts of surfactant prove to be perfectly acceptable with pharmaceutical forms such as tablets or gelatin capsules, whose sizes will remain compatible with oral administration.

In a preferred manner, solid pharmaceutical compositions of the invention, for example in tablet or gelatin capsule form, can contain from 200 to 400 mg of active principle calculated in the form of base and from 5% to 15%, more particularly 10%, by weight of nonionic hydrophilic surfactant relative to the active principle in base form.

For packaging in the form of powder in a unit sachet, from 1% to 50% by weight of nonionic hydrophilic surfactant relative to the active principle in base form may be used.

Besides the surfactant in question, the compositions in solid form according to the invention will comprise other pharmaceutical excipients generally used in the development of oral pharmaceutical forms.

These substances are entirely known to those skilled in the art, who can readily select them depending on the type of oral composition chosen.

As nonlimiting examples, mention may be made of binders, generally cellulose derivatives such as methylcellulose, hydroxyethylcellulose or methyl-hydroxypropylcellulose, or alternatively macrogols such as macrogol 6000; flow agents such as colloidal silica; vinylpyrrolidone polymers or copolymers such as polyvinylpyrrolidone; diluents such as lactose or mannitol; starches such as wheat starch or corn starch; lubricants such as magnesium stearate or sodium stearyl fumarate.

The compositions of the invention can be prepared by carrying out known processes involving, in particular, techniques of granulation via a wet or dry route, via fusion or via direct tabletting for the formation of tablets.

For example, tablets can be prepared by wet granulation by mixing together, at the initial stage, all of the ingredients, including the active principle and the surfactant, except for, however, the lubricant.

Operations of wetting with purified water, drying and sizing of the granule obtained, lubrication and tabletting or direct filling of gelatin capsules are then carried out.

According to variants of this method:

a) all of the ingredients, including the active principle, except for the surfactant and the lubricant, are mixed together at the initial stage and the process continues by operations of wetting with an aqueous solution of the surfactant, granulation, drying, sizing, lubrication and tabletting or direct filling of gelatin capsules, or b) all of the ingredients, including the active principle and the surfactant, except for the binder and the lubricant, are mixed together at the initial stage and the process then continues by operations of wetting with an aqueous solution of the binder, granulation, drying, sizing, lubrication and tabletting or direct filling of gelatin capsules.

These methods can also be modified by including a continuous granulation process which uses the fluidized airbed technique at the stage of the wetting operation.

In addition, it is also possible to use a process in which all of the ingredients are mixed together in the initial stage, except for the lubricant, which is heated to a temperature of about 60° C. to 65° C. Operations of hot granulation, sizing after cooling, lubrication and tabletting or direct filling of gelatin capsules are then carried out.

According to dry granulation techniques, all of the ingredients, including the active principle and the surfactant, except for the lubricant, are first mixed together and the process then continues with operations of screening, compacting, sizing, lubrication and tabletting or direct filling of gelatin capsules.

Finally, the process can be performed by direct tabletting using the following sequence of operations: mixing of the ingredients including the active principle and the surfactant, except the lubricant, followed by screening and mixing, then lubrication and finally tabletting or direct filling of gelatin capsules.

The characteristics and advantages of the oral compositions according to the invention will become apparent in the light of the description hereinbelow using specific oral compositions given by way of example with reference to the attached drawings.

I. Test of Maintenance in Solution at pH=6.7

A. Active Principle Alone

Solutions were prepared containing 2 mg/ml of dronedarone hydrochloride in hydrogenphosphate ($NaH_2PO_4$) buffered medium at pH=4.5 for 2 hours at 37° C. in the presence or absence of x % of nonionic hydrophilic surfactant to be studied, calculated on a weight basis relative to the active principle in base form.

This solution was then diluted to 1/10th in a neutral phosphate medium ($Na_{2\ HPO_4}+NaH_2PO_4$), the pH of the final solution being 6.7.

After 2 hours at 37° C., the solution was filtered through an Acrodisc® brand 5 μm filter and the active principle in solution was assayed by UV spectrometry.

| Surfactant | x % | % of dronedarone hydrochloride in solution |
|---|---|---|
| TWEEN ® 20 | 50 | 65 |
| TWEEN ® 40 | 50 | 63 |
| TWEEN ® 60 | 50 | 74 |
| TWEEN ® 80 | 50 | 69 |
| Synperonic ® PE/F68 | 50 | 74 |
| Synperonic ® PE/F87 | 50 | 75 |
| Synperonic ® PE/F127 | 50 | 95 |
| CREMOPHOR ® RH 40 | 50 | 64 |
| SOLUTOL ® HS 15 | 50 | 59 |
| Synperonic ® PE/F127 | 10 | 78 |
| Synperonic ® PE/F127 | 5 | 63 |
| — | — | 5 |

B. Active Principle in Tablet Form

Solutions were prepared containing 2 mg/ml of dronedarone hydrochloride (expressed in base form) in hydrogenphosphate ($NaH_2PO_4$) buffered medium at pH=4.5 or containing 2 mg/ml of amiodarone hydrochloride, in a buffered medium at pH=3.5.

These solutions were obtained by dissolving dronedarone hydrochloride tablets or amiodarone hydrochloride tablets containing or not containing 10% of poloxamer 407 (Synperonic® PE/F127), i.e.:

|  | Tablets | |
| --- | --- | --- |
|  | α (mg) | A (mg) |
| Dronedarone hydrochloride (corresponding to 400 mg of base) | 426 | 426 |
| Methylhydroxypropylcellulose | 12 | 12 |
| Lactose monohydrate | 63.6 | 63.6 |
| Modified corn starch | 60 | 60 |
| Polyvinylpyrrolidone | 30 | 30 |
| Anhydrous colloidal silica | 2.4 | 2.4 |
| Synperonic ® PE/F127 | — | 40 |
| Magnesium stearate | 6 | 6 |
|  | 600 | 640 |

|  | Tablets | |
| --- | --- | --- |
|  | β (mg) | B (mg) |
| Amiodarone hydrochloride | 200 | 200 |
| Lactose monohydrate | 71 | 71 |
| Modified corn starch | 66 | 66 |
| Crosslinked polyvinylpyrrolidone | 6 | 6 |
| Anhydrous colloidal silica | 2.4 | 2.4 |
| Synperonic ® PE/F127 | — | 20 |
| Magnesium stearate | 4.6 | 4.6 |
|  | 350 | 370 |

After 2 hours of dissolution at 37° C., these solutions are diluted to 1/10th in a neutral phosphate medium (Na$_2$HPO$_4$+NaH$_2$PO$_4$), the pH of the final solution being 6.7.

The test was then continued as described in paragraph A above and the following results were obtained:

|  | % of dronedarone hydrochloride in solution |
| --- | --- |
| Tablet α | 4.6 |
| Tablet A | 80 |

|  | % of amiodarone hydrochloride in solution |
| --- | --- |
| Tablet β | 55 |
| Tablet B | 100 |

These results show that, in tablets, the incorporation of 10% by weight of poloxamer 407, relative to the base dronedarone or to the amiodarone hydrochloride, makes it possible to maintain from 80% to 100% of active principle in solution for 2 hours.

II. Pharmacokinetic Tests

Comparative tests with dronedarone hydrochloride were carried out on 16 male volunteers, 8 of whom had been fasted and the other 8 not.

These tests were performed using tablets of the invention: one at 10% by weight of surfactant relative to the weight of dronedarone in base form (tablet A above), the other at 5% by weight of the same surfactant (tablet C below), i.e.:

| Tablet C | mg |
| --- | --- |
| Dronedarone hydrochloride (corresponding to 400 mg of base) | 426 |
| Methylhydroxypropylcellulose | 12 |
| Lactose monohydrate | 63.6 |
| Modified corn starch | 60 |
| Polyvinylpyrrolidone | 30 |
| Anhydrous colloidal silica | 2.4 |
| Synperonic ® PE/F127 | 20 |
| Magnesium stearate | 6 |
|  | 620 | compared with compositions free of nonionic hydrophilic surfactant, i.e.:

a) tablet α above b) gelatin capsule having a composition of formulation:

|  | mg |
| --- | --- |
| Dronedarone hydrochloride (corresponding to 200 mg of base) | 213 |
| Modified corn starch | 86.2 |
| Lactose monohydrate | 129.2 |
| Talc | 48 |
| Anhydrous colloidal silica | 1.2 |
| Magnesium stearate | 2.4 |
|  | 480 |

Each of these volunteers received a single dose of dronedarone hydrochloride equivalent to 800 mg of base in the form of the above gelatin capsule, of tablet α, of tablet A or of tablet C, each single dose being separated from the following one by an interval of 7 days.

Plasmatic dronedarone assays were then carried out on each individual 0, 1, 2, 3, 4, 5, 6, 7, 10, 12, 16 and 24 hours after administration and the maximum concentrations of this active principle (C max in ng/ml) were noted, as well as the area under the curves defined by the concentration of the active principle as a function of time (AUC in ng.h/ml).

This procedure was repeated in a second series of tests carried out on the same two groups of 8 alternate volunteers, i.e. the 8 fasted volunteers carrying out the test while not fasted, and vice versa.

BRIEF DESCRIPTION OF THE DRAWINGS

The results obtained when fasted are reproduced in the attached FIG. 1 and those obtained while not fasted appear in the attached FIG. II, in which:

a) the curve referred to as "gelatin capsule" represents the average plasmatic concentration obtained with the composition in the form of a gelatin capsule b) the curve referred to as "tablet α" represents the average plasmatic concentration obtained with the tablet α c) the curve referred to as "tablet A" represents the average plasmatic concentration obtained with the tablet A containing 10% of Synperonic® PE/F127 surfactant d) the curve referred to as "tablet C" represents the average plasmatic concentration obtained with tablet C containing 5% of Synperonic® PE/F127 surfactant.

Figure 1:
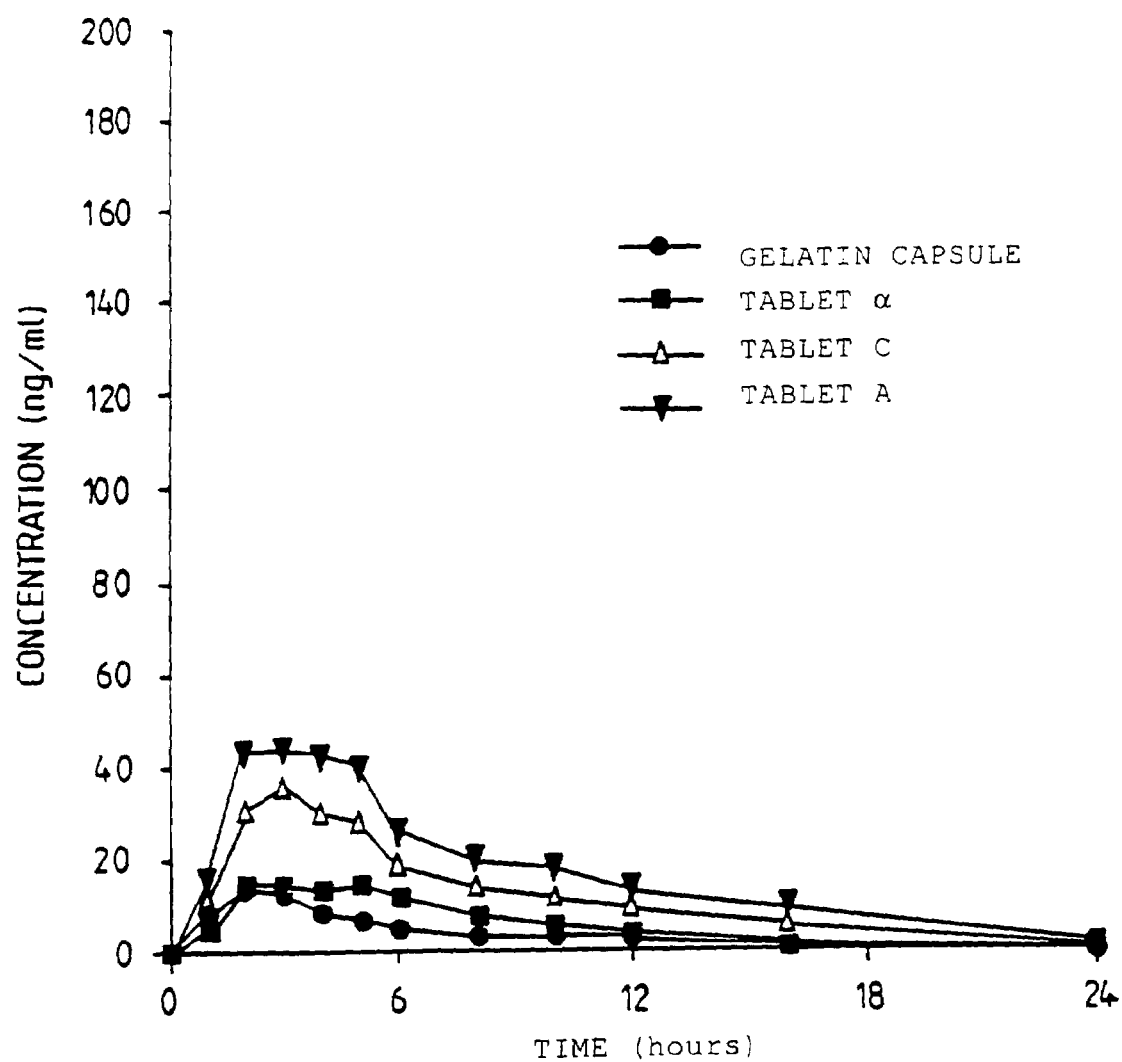
Figure 2:
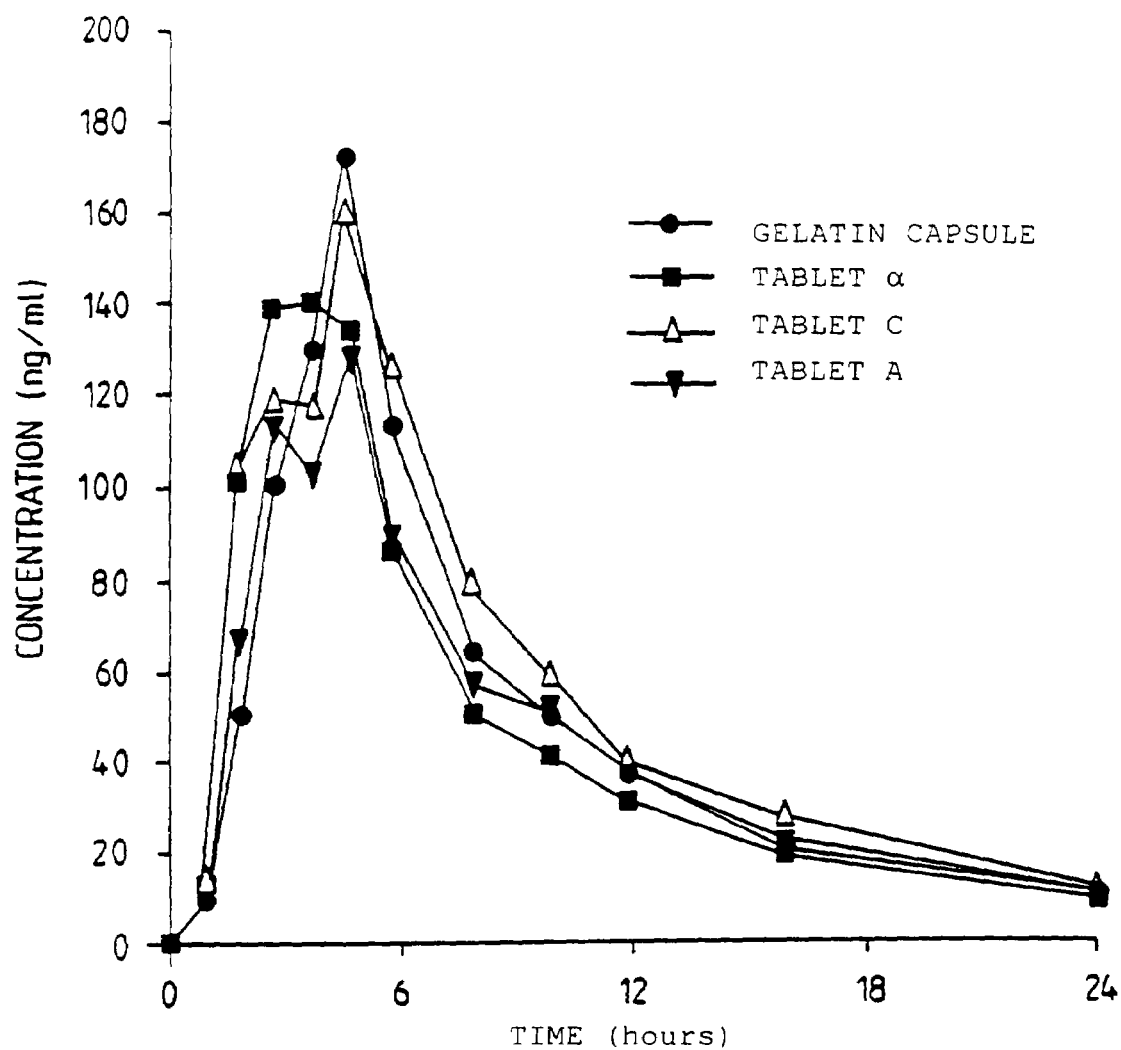

From these curves, it is possible in particular:
1) to deduce that the presence of the surfactant increases the fasted bioavailability of the active principle.
2) to draw up the following comparative tables from the results of the C max and AUC values obtained with each formulation in the non-fasted volunteers compared with the corresponding results in the fasted volunteers, relative to 1:

TABLE I

| Ratio of the C max values | Treatment | | | |
|---|---|---|---|---|
| | Gelatin capsule | Tablet α | Tablet C | Tablet A |
| Fasted | 1 | 1 | 1 | 1 |
| Not fasted | 12.5 | 10.3 | 4.8 | 2.7 |

TABLE II

| Ratio of the AUC values | Treatment | | | |
|---|---|---|---|---|
| | Gelatin capsule | Tablet α | Tablet C | Tablet A |
| Fasted | 1 | 1 | 1 | 1 |
| Not fasted | 16.7 | 8.9 | 5.3 | 3.2 |

These tables show that the surfactant is capable of reducing by a factor of 2 to 5 the variations in maximum plasmatic concentrations of active principle obtained in non-fasted individuals compared with fasted individuals (Table I).

Similarly, it may be concluded that the large variations in bioavailability recorded with surfactant-free compositions could be reduced by a factor of 1.5 to 5 (Table II).

The following non-limiting examples illustrate the invention.

EXAMPLE 1

Dronedarone Hydrochloride Tablet
Dronedarone hydrochloride tablets of the formulation below were prepared:

| Ingredients | mg | % |
|---|---|---|
| Dronedarone hydrochloride (corresponding to 400 mg of base) | 426 | 65.5 |
| Methylhydroxypropylcellulose | 21.1 | 3.25 |
| Lactose monohydrate | 46.55 | 7.2 |
| Modified corn starch | 45.5 | 7 |
| Polyvinylpyrrolidone | 65 | 10 |
| Poloxamer 407 | 40 | 6.15 |
| Anhydrous colloidal silica | 2.6 | 0.4 |
| Magnesium stearate | 3.25 | 0.5 |
| | 650 | 100 | by applying the process below:

After screening, 724.2 g of dronedarone hydrochloride, 35.9 g of methylhydroxypropylcellulose, 79.1 g of lactose monohydrate, 77.4 g of corn starch and 82.9 g of polyvinylpyrrolidone are mixed together.

The mixture is moistened with 68 g of poloxamer 407 (Synperonic® PE/F127) as a solution in 408 g of purified water, and this mixture is granulated. The wet mass is dried at a temperature of about 50° C. and is sized on screens with a mesh size of 1.250 mm. 27.6 g of polyvinylpyrrolidone, 4.4 g of anhydrous colloidal silica and 5.5 g of magnesium stearate are mixed with the granule thus sized and the final mixture is then tabletted in a proportion of 650 mg per unit.

EXAMPLE 2

Dronedarone Hydrochloride Tablet
Dronedarone hydrochloride tablets of identical formulation to that of Example 1 were prepared by applying the process below:

After screening, 724.2 g of dronedarone hydrochloride, 35.9 g of methylhydroxypropylcellulose, 79.1 g of lactose monohydrate, 77.4 g of corn starch, 82.9 g of polyvinylpyrrolidone and 68 g of poloxamer 407 (Synperonic® PE/F127) are mixed together. The mixture is then moistened with purified water, after which the process is carried out in the same way as in Example 1 in order to obtain tablets with a weight of 650 mg per unit.

EXAMPLE 3

Dronedarone Hydrochloride Tablet
Dronedarone hydrochloride tablets of identical formulation to that of Example 1 were prepared by applying the process below:

After screening, 724.2 g of dronedarone hydrochloride, 79.1 g of lactose monohydrate, 77.4 g of corn starch, 82.9 g of polyvinylpyrrolidone and 68 g of poloxamer 407 (Synperonic® PE/F127) are mixed. The mixture is moistened with 35.9 g of methylhydroxypropylcellulose as a solution in 408 g of purified water and this mixture is granulated. The wet mass is dried at a temperature of about 50° C. and is sized on a screen with a mesh size of 1.250 mm. 27.6 g of polyvinylpyrrolidone, 4.4 g of anhydrous colloidal silica and 5.5 g of magnesium stearate are mixed with the granule thus sized and the final mixture is then tabletted in a proportion of 650 mg per unit.

EXAMPLE 4

Dronedarone Hydrochloride Tablet
Dronedarone hydrochloride tablets of the formulation below were prepared:

| Ingredients | mg | % |
|---|---|---|
| Dronedarone hydrochloride (corresponding to 400 mg of base) | 426 | 65.5 |
| Microcrystalline cellulose | 65 | 10 |
| Anhydrous colloidal silica | 2.6 | 0.4 |
| Anhydrous lactose | 42.65 | 6.6 |
| Polyvinylpyrrolidone | 13 | 2 |
| Poloxamer 407 | 40 | 6.15 |
| Macrogol 6000 | 57.5 | 8.85 |
| Magnesium stearate | 3.25 | 0.5 |
| | 650 | 100 | by carrying out the process below:

After screening, 724.2 g of dronedarone hydrochloride, 110.5 g of microcrystalline cellulose, 2.2 g of anhydrous colloidal silica, 72.5 g of anhydrous lactose, 22.1 g of polyvinylpyrrolidone, 68 g of poloxamer 407 (Synperonic® PE/F127) and 97.8 g of macrogol 6000 are mixed together. The temperature of the mixture is raised to 65° C. in a thermostatically-controlled tank, with slow stirring. This mixture is granulated with fast stirring, cooled to room temperature and then sized. 2.2 g of anhydrous colloidal silica and 5.5 g of magnesium stearate are then mixed with the sized granule and the final mixture is tabletted in a proportion of 650 mg per unit.

This granulation process can also be carried out in apparatus with a fluidized airbed.

EXAMPLE 5

Dronedarone Hydrochloride Tablet

Dronedarone hydrochloride tablets of identical formulation to that of Example 4 were prepared by applying the process below:

After sizing, 724.2 g of dronedarone hydrochloride, 110.5 g of microcrystalline cellulose, 2.2 g of anhydrous colloidal silica, 72.5 g of anhydrous lactose, 22.1 g of polyvinylpyrrolidone, 68 g of molten poloxamer 407 (Synperonic® PE/F127) and 97.8 g of molten macrogol 6000 are mixed together.

The process is then carried out in the same way as in Example 4, in order to obtain tablets with a weight of 650 mg per unit.

EXAMPLE 6

Dronedarone Hydrochloride Tablet

Dronedarone hydrochloride tablets of identical formulation to that of Example 4, but after replacing the macrogol 6000 with an equivalent amount of poloxamer 407, were prepared by applying the process below:

After sizing, 724.2 g of dronedarone hydrochloride, 110.5 g of microcrystalline cellulose, 2.2 g of anhydrous colloidal silica, 72.5 g of anhydrous lactose, 22.1 g of polyvinylpyrrolidone and 166.7 g of poloxamer 407 (Synperonic® PE/F127) are mixed together.

The process is then performed in the same way as in Example 4, in order to obtain tablets with a weight of 650 mg per unit.

EXAMPLES 7 and 8

Following the processes described above, tablets of the formulation below were prepared:

a)

| Ingredients | mg | % |
|---|---|---|
| Dronedarone hydrochloride (corresponding to 400 mg of base) | 426 | 65.6 |
| Microcrystalline cellulose | 26 | 4 |
| Corn starch | 45.5 | 7 |
| Polyvinylpyrrolidone | 65 | 10 |
| Poloxamer 407 | 40 | 6.1 |
| Anhydrous colloidal silica | 2.6 | 0.4 |
| Magnesium stearate | 3.25 | 0.5 |
| Lactose monohydrate | 41.65 | 6.4 |
| | 650 | 100 | b)

| Ingredients | mg | % |
|---|---|---|
| Dronedarone hydrochloride (corresponding to 200 mg of base) | 213 | 65.6 |
| Microcrystalline cellulose | 13 | 4 |
| Corn starch | 22.75 | 7 |
| Polyvinylpyrrolidone | 32.5 | 10 |
| Poloxamer 407 | 20 | 6.1 |
| Anhydrous colloidal silica | 1.3 | 0.4 |
| Magnesium stearate | 1.625 | 0.5 |
| Lactose monohydrate | 20.825 | 6.4 |
| | 325 | 100 |

The invention claimed is:

1. A solid pharmaceutical composition in tablet form for oral administration comprising a benzofuran derivative with antiarrhythmic activity selected from the group consisting of dronedarone and amiodarone, or a pharmaceutically acceptable salt thereof, as an active principle, and a pharmaceutically acceptable nonionic hydrophilic surfactant selected from poloxamers, optionally in combination with one or more pharmaceutical excipients, said nonionic hydrophilic surfactant being present in a proportion of from 5% to 15% by weight of the active principle in base form, provided that the pharmaceutical composition does not contain a polysorbate surfactant.

2. A pharmaceutical composition according to claim 1 wherein the pharmaceutically acceptable salt is the hydrochloride.

3. A pharmaceutical composition according to claim 2, wherein the benzofuran derivative is dronedarone hydrochloride.

4. A pharmaceutical composition according to claim 2, wherein the benzofuran derivative is amiodarone hydrochloride.

5. A pharmaceutical composition according to claim 1 wherein the nonionic hydrophilic surfactant is selected from the group consisting of poloxamer 124, poloxamer 188, poloxamer 237, poloxamer 338, and poloxamer 407.

6. A pharmaceutical composition according to claim 5 wherein the nonionic hydrophilic surfactant is poloxamer 407.

7. A pharmaceutical composition according to claim 6 wherein the benzofuran derivative is dronedarone hydrochloride.

8. A pharmaceutical composition according to claim 6 wherein the benzofuran derivative is amiodarone hydrochloride.

9. A pharmaceutical composition according to claim 5 containing from 50 to 500 mg of active principle.

10. A pharmaceutical composition according to claim 9, containing from 200 to 400 mg of active principle.

11. A pharmaceutical composition according to claim 10, containing from 200 to 400 mg of active principle, calculated in base form, and 10% by weight of nonionic hydrophilic surfactant relative to the active principle in base form.

12. A pharmaceutical composition according to claim 11 wherein the active principle is selected from the group consisting of amiodarone hydrochloride and dronedarone hydrochloride or a pharmaceutically acceptable salt thereof.

13. A pharmaceutical composition according to claim 12 wherein the nonionic hydrophilic surfactant is poloxamer 407.

14. A pharmaceutical composition according to claim 13 wherein the active principle is dronedarone hydrochloride.

* * * * *

UNITED STATES PATENT AND TRADEMARK OFFICE
CERTIFICATE OF CORRECTION

PATENT NO. : 7,323,493 B1 Page 1 of 1
APPLICATION NO. : 09/446601
DATED : January 29, 2008
INVENTOR(S) : Abramovici et al.

It is certified that error appears in the above-identified patent and that said Letters Patent is hereby corrected as shown below:

Column 1, line 1: Insert the following text: -- Cross Reference to Related Applications --.

Column 1, line 2: Insert the following text: -- This application is a 35 U.S.C. § 371 application of PCT International Application No. PCT/FR98/01285 filed June 19, 1998. --.

Column 4, line 37: "$Na_{2\ HPO4}$" should read as -- $Na_2HPO_4$ --.

Column 4, line 42: Insert the following text: -- The following results were thus obtained: --.

Claim 3, line 29: "claim 2" should read as -- claim 1 --.

Claim 4, line 32: "claim 2" should read as -- claim 1 --.

Claim 12, line 59: Cancel the following text: "or a pharmaceutically acceptable salt thereof".

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,323,493 B1　　　　　　　　　　　　　　　　　　　　　Page 1 of 1
APPLICATION NO. : 09/446601
DATED : January 29, 2008
INVENTOR(S) : Abramovici et al.

It is certified that error appears in the above-identified patent and that said Letters Patent is hereby corrected as shown below:

Column 1, line 1:　Insert the following text: -- Cross Reference to Related Applications --.

Column 1, line 2:　Insert the following text: -- This application is a 35 U.S.C. § 371 application of PCT International Application No. PCT/FR98/01285 filed June 19, 1998. --.

Column 4, line 37:　"$Na_{2\,HPO4}$" should read as -- $Na_2HPO_4$ --.

Column 4, line 42:　Insert the following text: -- The following results were thus obtained: --.

Column 10, Claim 3, line 29:　"claim 2" should read as -- claim 1 --.

Column 10, Claim 4, line 32:　"claim 2" should read as -- claim 1 --.

Column 10, Claim 12, line 59:　Cancel the following text: "or a pharmaceutically acceptable salt thereof".

This certificate supersedes the Certificate of Correction issued June 17, 2008.

Signed and Sealed this

Twenty-second Day of July, 2008

JON W. DUDAS
*Director of the United States Patent and Trademark Office*